US006814723B2

(12) United States Patent
Moder et al.

(10) Patent No.: US 6,814,723 B2
(45) Date of Patent: Nov. 9, 2004

(54) LABIAL PRODUCT SYSTEM TO MAINTAIN A TREATMENT AGENT

(75) Inventors: Susan J. Moder, Appleton, WI (US); Richard W. Kubalek, Appleton, WI (US); William G. Reeves, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 37 days.

(21) Appl. No.: 10/208,586

(22) Filed: Jul. 29, 2002

(65) Prior Publication Data

US 2004/0019335 A1 Jan. 29, 2004

(51) Int. Cl.[7] ................................................. A61F 13/20
(52) U.S. Cl. ..................................... 604/385.17; 604/12
(58) Field of Search .......................... 604/358, 385.17, 604/11–18, 904

(56) References Cited

U.S. PATENT DOCUMENTS

| | | |
|---|---|---|
| 4,595,392 A | 6/1986 | Johnson et al. |
| 4,743,245 A | 5/1988 | Lassen et al. |
| 5,350,067 A | 9/1994 | Beltran |
| 5,827,251 A | 10/1998 | Moder et al. |
| 5,891,127 A | 4/1999 | Moder et al. |
| 5,964,741 A | 10/1999 | Moder et al. |
| 5,986,165 A | 11/1999 | Moder et al. |
| 5,988,386 A | 11/1999 | Morrow |
| 6,183,456 B1 | 2/2001 | Brown et al. |
| 2002/0026140 A1 * | 2/2002 | McNamara .................. 604/12 |
| 2002/0115976 A1 | 8/2002 | Fleming |
| 2003/0114823 A1 | 6/2003 | Bosselaar et al. |
| 2003/0120225 A1 * | 6/2003 | Everhart et al. ............ 604/285 |

FOREIGN PATENT DOCUMENTS

WO    WO 02/17844 A2    3/2002

OTHER PUBLICATIONS

Gray, Henry, *Anatomy of the Human Body*, vol. II, Thirtieth American Edition, published by Lea and Febiger, 1985, pp. 1571–1581.

* cited by examiner

*Primary Examiner*—John J. Calvert
*Assistant Examiner*—Linh Truong
(74) *Attorney, Agent, or Firm*—Paul Y. Yee

(57) ABSTRACT

A process and system for maintaining a position of a feminine-care treatment (86) includes a providing of an operative quantity of at least one feminine-care treatment material (86), and a depositing of the treatment material into a vulva-vaginal area of a recipient, female user. A maintenance article, such as provided by an interlabial device (40), is placed into an interlabial space of the user. The maintenance article (40) is configured to operatively impede an undesired movement of the treatment material (86) from the vulva-vaginal area when the interlabial device is placed in the interlabial space of the user. In a particular aspect, the maintenance article (40) can include a liquid-permeable topsheet layer (62), and a pliable core (66) which operatively joined to the topsheet layer (62). In another aspect, the maintenance article (40) can include a backsheet layer (64) which is joined to the topsheet layer (62), and can have the pliable core member (66) positioned between the topsheet layer (62) and the backsheet layer (64). Still another aspect can include a bundling mechanism (90) for operatively holding the treatment material (86) and the interlabial device (40) in a convenient system-assembly (88).

10 Claims, 13 Drawing Sheets

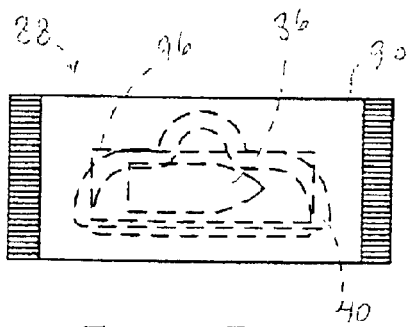
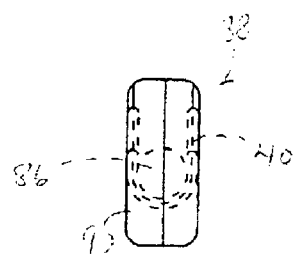
FIG. 17   FIG. 17A
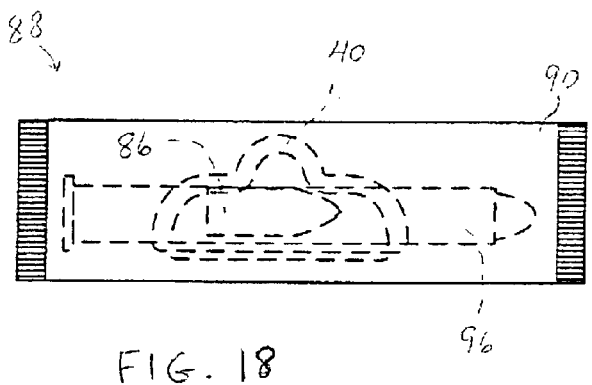
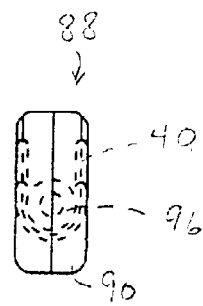
FIG. 18   FIG. 18A
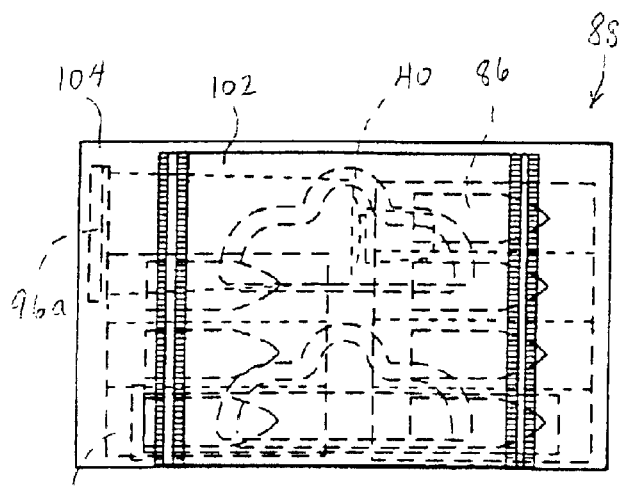
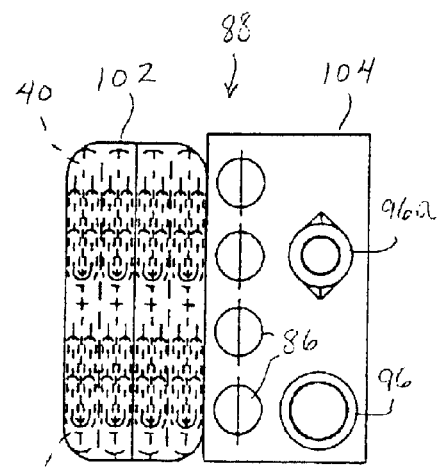
FIG. 19   FIG. 19A

LABIAL PRODUCT SYSTEM TO MAINTAIN A TREATMENT AGENT

FIELD

The present invention relates generally to a system for operatively maintaining an appointed location of a selected treatment agent in the crotch region of a user. More particularly, the present invention relates to a system which includes an article, such as a labial pad, that can be configured for disposition within the vestibule of a female wearer and can be employed to maintain a desired location of a selected treatment agent.

BACKGROUND

A broad manner and wide variety of absorbent articles configured for the absorption of bodily exudates such as menstrual fluid are well known. With respect to feminine hygiene, the art has offered two basic types of feminine hygiene protection: sanitary napkins, developed for external wear about the pudendal region, and tampons, developed for residence within the vaginal cavity and interruption of menstrual flow therefrom. Hybrid feminine hygiene protection devices, attempting to merge the structural features of both within a single type of device, have also been proposed, but have not seen a meaningful measure of acceptance. The ability to realize appropriate advantages has been overshadowed by the more demonstrable perpetuation of structural and functional disadvantages. Other less intrusive devices have also been proposed. Such devices have been known as labial or interlabial devices, and characterized as having a portion which at least partially resides external of the wearer's vestibule. Other, even smaller devices that may be worn interlabially by a female wearer, have also been produced. Additionally, there have been arrangements which combine the use of labial or interlabial devices with the use of other absorbent, feminine hygiene articles.

Conventional feminine hygiene systems, such as those described above, have failed to recognize the significance of maintaining a treatment at a desired body-location of a female. For example, the conventional systems for applying a treatment material or agent have permitted an excessive movement of the treatment away from desired locations. As a result, such conventional systems have experienced reduced efficacy, increased cost, greater inconvenience, and excessive discomfort to the wearer.

BRIEF DESCRIPTION

The present inventors have recognized the deficiencies and problems inherent in the prior art, and in response, have conducted intensive research in developing innovative systems that employ labial pads.

Generally stated, a process for maintaining a feminine-care treatment comprises a providing of an operative quantity of at least one feminine-care treatment material, and a depositing of the treatment material into a vulva-vaginal area of a recipient, female user. A maintenance article is placed into an interlabial space of the user. The maintenance article is arranged to operatively impede a movement of the treatment material from the vulva-vaginal area when the interlabial device is placed in the interlabial space of the user.

In another aspect, a system for maintaining a feminine care treatment includes an operative quantity of at least one feminine care treatment material configured for placement in a vulva-vaginal area of a recipient, female user, and a maintenance article for placement into an interlabial space of the user. The maintenance article is configured to operatively impede a movement of the treatment material from the user's vulva-vaginal area when the interlabial device is placed into the interlabial space of the user. In a particular aspect, the system can include a bundling mechanism for holding the treatment material and the maintenance article in a convenient system-assembly.

By incorporating its various features, the process and system of the invention can better maintain a selected treatment or combination of treatments at a desired body-location of a female. For example, the process and system of the invention can better reduce excessive movement of the treatment away from desired locations. As a result, the invention can help to increase the efficacy of the selected treatment, provide greater convenience and comfort to the user, and reduce the cost of the treatment.

DRAWINGS

The foregoing and other features, aspects, configurations and advantages of the present invention will become better understood with regard to the following description, claims and accompanying drawings where:

FIG. 1 representatively shows a simplified anatomical cross-sectional view of a human female illustrating the external genitalia.

FIG. 2 representatively shows a simplified anatomical cross-sectional view of a human female illustrating the environment for a maintenance article, such as provided by a labial pad.

FIG. 3 representatively shows a simplified view illustrating the positioning of an inserted maintenance article having a notch located on that portion of the periphery thereof that is intended to be situated nearest the clitoris of a human female.

FIG. 4 representatively shows a top view illustrating a version of a maintenance article arranged in a generally flat condition.

FIG. 5 representatively shows cross-sectional view of the maintenance article illustrated in FIG. 4 taken along line 5—5 thereof.

FIG. 6 representatively shows a cross-sectional view illustrating another version of a maintenance article having a cover layer, a backsheet layer and a pliable component or member sandwiched between the cover and backsheet layers.

FIG. 7 representatively shows a top view illustrating an embodiment of a notch situated on the periphery of a maintenance article which is arranged in a generally flat condition.

FIG. 8 representatively shows a top view illustrating another embodiment of a notch situated on the periphery of yet another version of a maintenance article which is arranged in a generally flat condition and.

FIG. 9 representatively shows a top view illustrating yet another embodiment having a plurality of notches situated on the periphery of still another version of a maintenance article which is arranged in a generally flat condition and.

FIG. 10 representatively shows a top view illustrating still another embodiment having a plurality of notches situated on the periphery of a further version of a maintenance article which is arranged in a generally flat condition and.

FIG. 11 representatively shows a cross-sectional view illustrating yet a further version of a maintenance article.

FIG. 12 representatively shows cross-sectional view illustrating the version of FIG. 12 in a selected, substantially folded position.

FIG. 17 shows a representative system-assembly which has an individual maintenance article, and at least one quantity or dosage of treatment material.

FIG. 17A shows a representative end view of the system-assembly illustrated in FIG. 17.

FIG. 18 shows a representative system-assembly which is arranged to include an individual maintenance article, an applicator, and an individual quantity or dosage of a selected treatment material.

FIG. 18A shows a representative end view of the system-assembly illustrated in FIG. 18.

FIG. 19 shows a representative system-assembly which is configured to include a plurality of individual, maintenance articles which are segregated in a first sub-container, a plurality of quantities or dosages of the treatment material which are separately held in a second sub-container, and at least one applicator.

FIG. 19A shows a representative, partially cut-away, end view of the system-assembly illustrated in FIG. 19.

DETAILED DESCRIPTION

Figure 1:
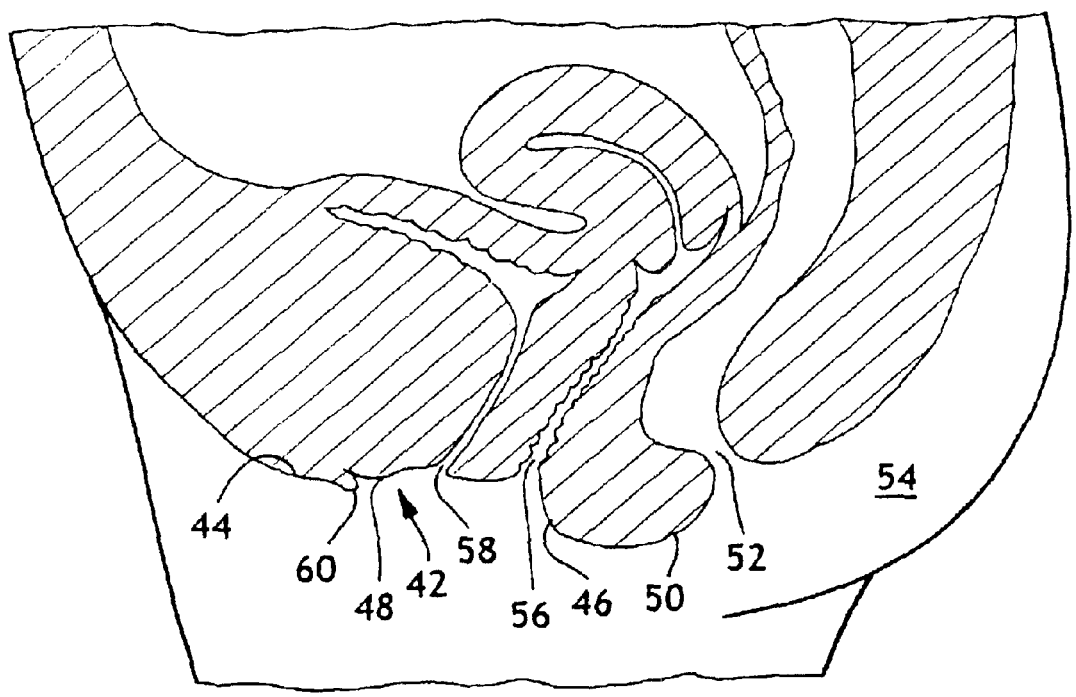

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof. It should also be noted that in each of the Figures of the drawings, similar parts are identified with like reference characters.

Figure 2:
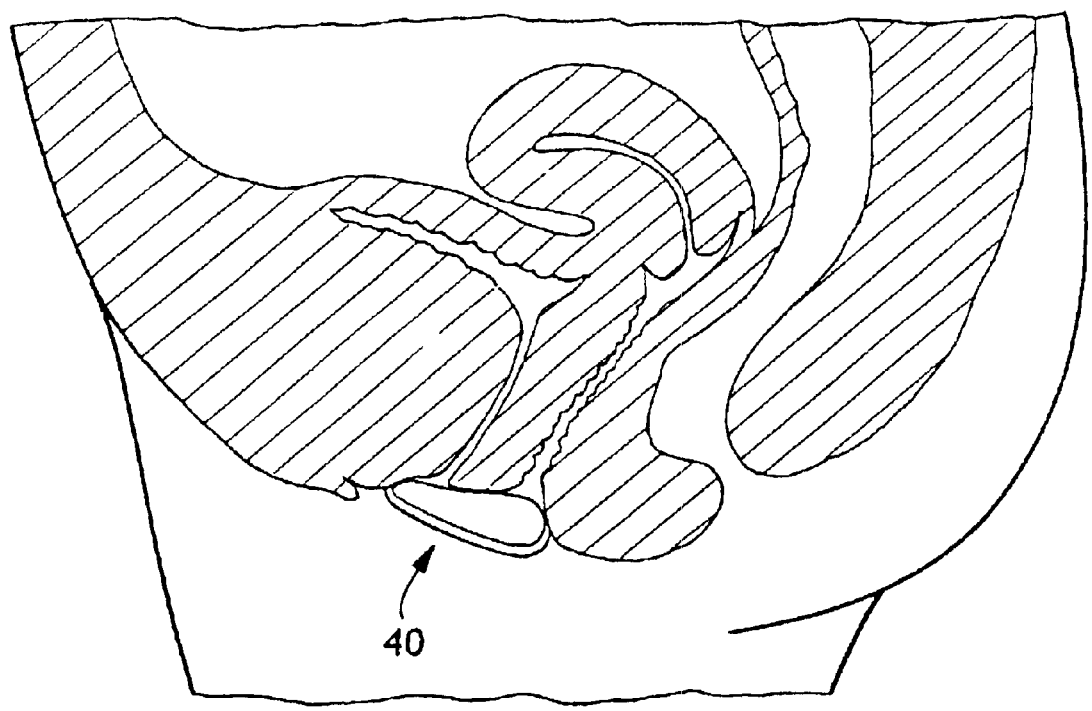

With reference to FIGS. 1 and 2, the vulva refers generally to the external female genitalia, including the labia minora 59, labia majora 61, clitoris 60 and vestibule 42. The vestibule 42 is considered to be the region defined within the labia beginning at about a point lying caudally from the anterior labial commissure 44, extending rearward to the posterior labial commissure 46 and bounded inwardly by the floor 48 of the vestibule. One of skill in the art fully understands that there is a wide range of variation among women with respect to the relative size and shape of labia minora 59 and labia majora 61 as the same interrelatedly define the contour of the vestibule 42. For purposes of the present description, however, such differences will not specifically be addressed, it being recognized that in any event the disposition of the maintenance article into the vestibule 42 will necessitate placement between the labia majora 61 regardless of any such consideration respecting the labia minora 59. Lying caudally of the vestibule 42 is the perineum 50 which leads to the anus 52 in the region of the buttocks 54. Within the vestibule 42 itself is located the principal urogenital members which, for purposes pertinent here, are constituted of the vaginal orifice 56, the urethral orifice 58, and the clitoris 60. Given the foregoing simplified review of this anatomical region, and to facilitate the present description, the vestibule 42 will be considered generally to be the region between the posterior labial commissure 46 and the clitoris 60, for convenience. For a more comprehensive description of this portion of the human female anatomy, however, reference can be made to *Anatomy of the Human Body* by Henry Gray, Thirtieth American Edition Carmine D. Clemente ed., Lea & Febiger, 1985 at 1571–1581.

Figure 3:
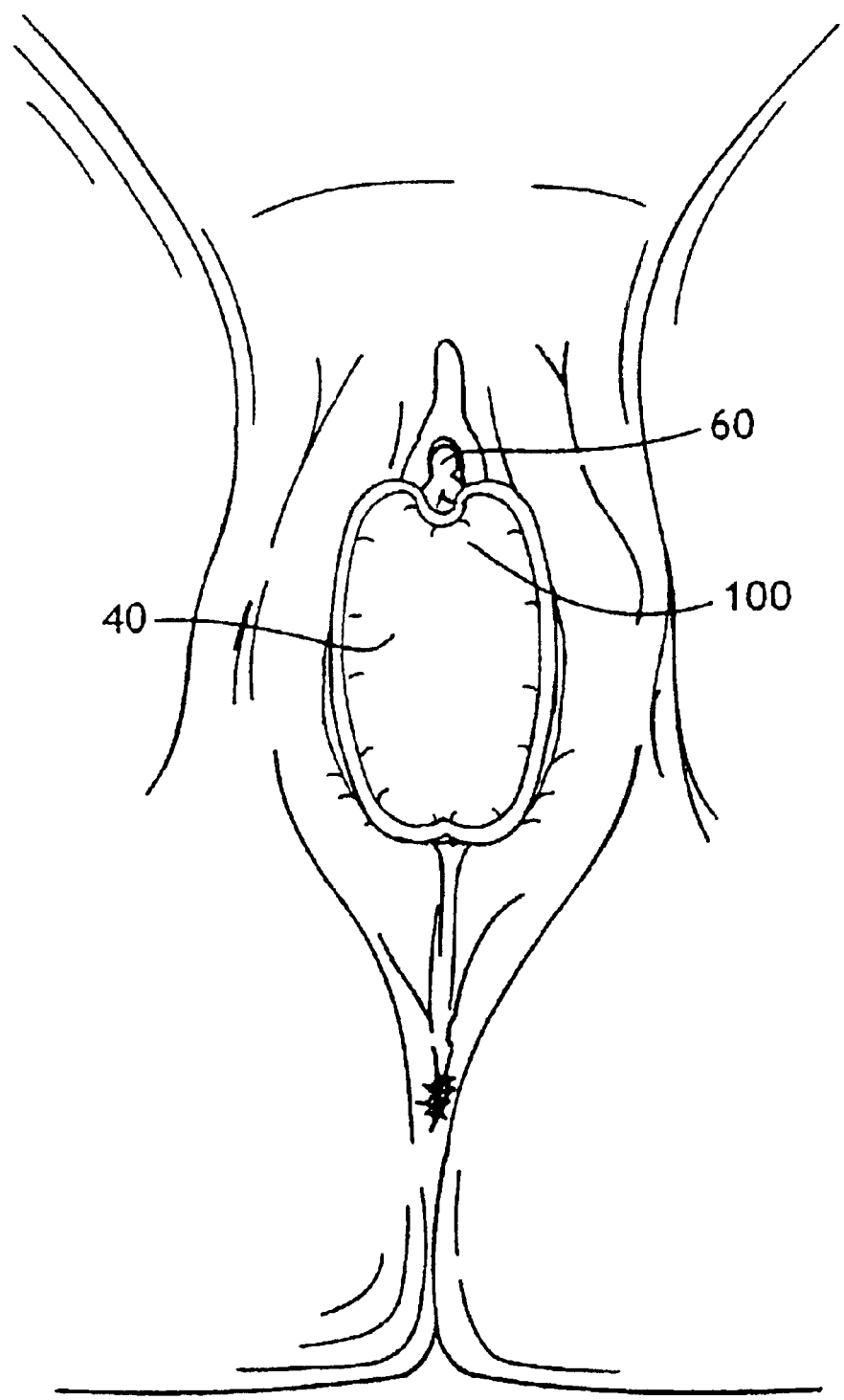

FIG. 3 diagrammatically illustrates a representative maintenance article, such as provided by a labial pad or other interlabial device 40, which is shown in a substantially unfolded or flat configuration prior to disposition within the vestibule of a wearer. The interlabial device may optionally include at least one absorbent component. Additionally, the interlabial device can be configured for disposition in between the labia majora, and can be configured to extend at least partially into the vestibule 42 of a female wearer during use.

The maintenance article, such as provided by the labial pad or other interlabial device 40, can be disposed at least partially within the vestibule 42 to operatively occlude the vestibule region and to operatively block or otherwise operatively restrict an undesired movement of material from the vulva-vaginal region of a female user. Desirably, the interlabial device or other maintenance article can be disposed substantially entirely within the vestibule region. The maintenance article may optionally be configured to provide an absorbent article which can be employed to provide for a desired intake and retention of a selected liquid, such as menstrual fluid emitted from the vaginal orifice 56. Additionally, the maintenance article may optionally serve as a type of incontinence device for the absorption and storage of urine, as may be desired to address minor, female incontinence. In a desired arrangement, the maintenance article is configured to operatively impede an undesired movement of a selected treatment material from the vulva-vaginal area, when the interlabial device is placed in the interlabial space of the user/wearer. In a particular feature, the maintenance article can be configured to be operatively occlusive and substantially nonabsorbent at least with respect to the selected treatment, and may be operatively permeable and absorbent with respect to ordinary bodily fluids, such as urine, vaginal fluids or the like.

Examples of known interlabial devices are described in U.S. Pat. No. 4,595,392 entitled INTERLABIAL PAD by Russell L. Johnson et al. which was issued Jun. 17, 1986; and in U.S. Pat. No. 4,743,245 entitled LABIAL SANITARY PAD by Frederich O. Lassen et al. which was issued May 10, 1988. The entire disclosures of these documents are incorporated herein by reference in a manner that is consistent herewith.

Interlabial pads are also described in U.S. patent application Ser. No. 10/036,990 entitled LABIAL PAD HAVING A NOTCH by James J. Hlaban et al. which was filed Dec. 31, 2001 (attorney docket No. 17,694); and in U.S. patent application Ser. No. 10/036,635 entitled LABIAL PAD HAVING A NOTCH by Ronald L. Edens et al. which was filed Dec. 31, 2001 (attorney docket No. 17,698). The entire disclosures of these documents are incorporated herein by reference in a manner that is consistent herewith.

Figure 4:
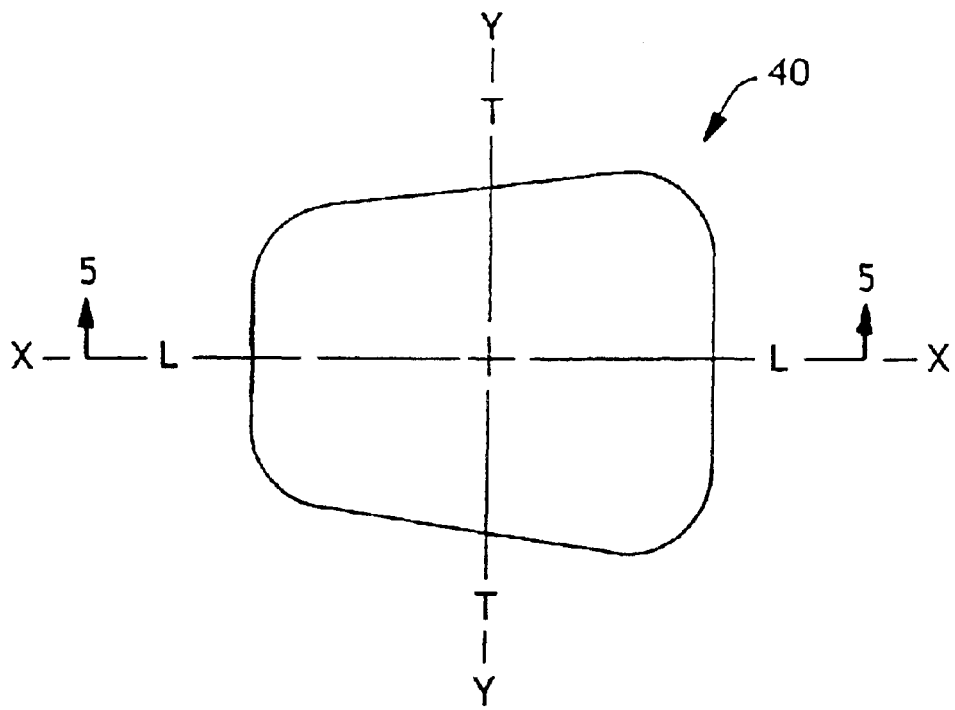
Figure 5:
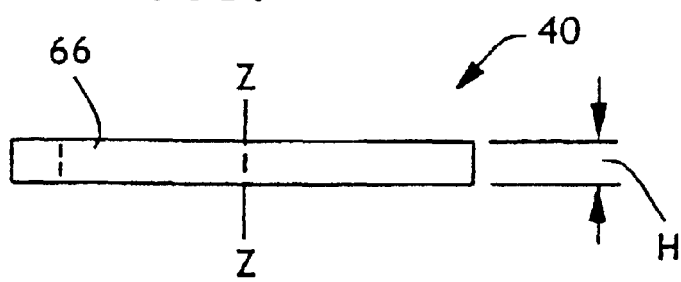

As illustrated in FIG. 4, the representative maintenance article (e.g. the interlabial device 40) can have a principal longitudinal axis (L) which generally runs along the x-direction. As used herein, the term "longitudinal" refers to a line, axis or direction which lies in the general plane of the maintenance article, and when the maintenance article is in use, is generally aligned with (e.g., approximately parallel to) a vertical plane that bisects a standing female wearer into left and right body halves. The longitudinal direction is generally illustrated in FIG. 4 by the x-axis. The maintenance article also has a principal transverse axis (T). The terms "transverse," "lateral" or "y-direction" as used herein generally refer to a line, axis or direction that is generally perpendicular to the longitudinal direction. The lateral direction is generally illustrated in FIG. 4 by the y-axis, and typically lies generally parallel to a representative plane of the article. The "z-direction" is typically a line, axis or direction generally parallel to the vertical plane described above, and is generally perpendicular to both the longitudinal (x-axis) and transverse (y-axis) directions. The z-direction is generally illustrated in FIG. 5 by the z-axis. The term "upper" refers generally to an orientation directed toward the wearer's head, while the terms "lower" or "downwardly" refer generally to an orientation directed toward the wearer's feet. For purposes of discussion herein, each layer of the maintenance article, e.g., a cover 62, a backsheet or baffle 64 and/or a pliable member 66 (e.g. FIG. 6), has an upper or body-facing surface and a lower surface also described as the surface opposed to the upper or body-facing surface. The pliable component 66 can be sufficiently flexed, molded, folded and/or shaped to provide a desired resiliency or other pliability which operatively allows a selective configuring of the maintenance article for its intended use by an individual person. In a particular aspect, the pliable component can be selectively shaped for interlabial placement in the vestibule region of the wearer, and can be selectively reconfigured by the individual wearer to provide a customized placement and fit of the maintenance article in the interlabial space of the wearer. As a result, the contours of the pliable member and the maintenance article can be tailored to more effectively match the body contours of the individual wearer, and can be customized to provide a tailored fit that can more effectively maintain the desired location of the selected treatment material. The pliable component 66 may optionally have a selected level of absorbent capacity, and may be configured to provide an operative, absorbent body or absorbent core.

Figure 6:
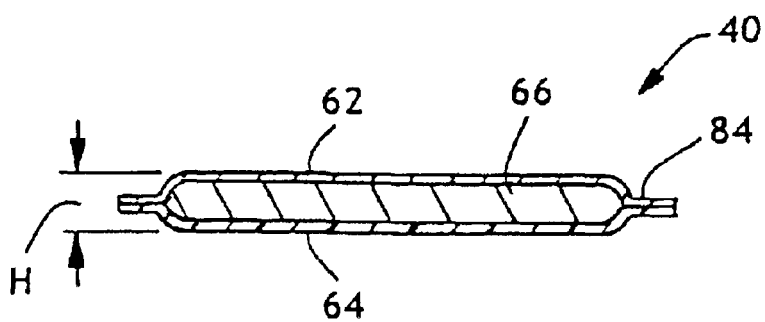
Figure 7:
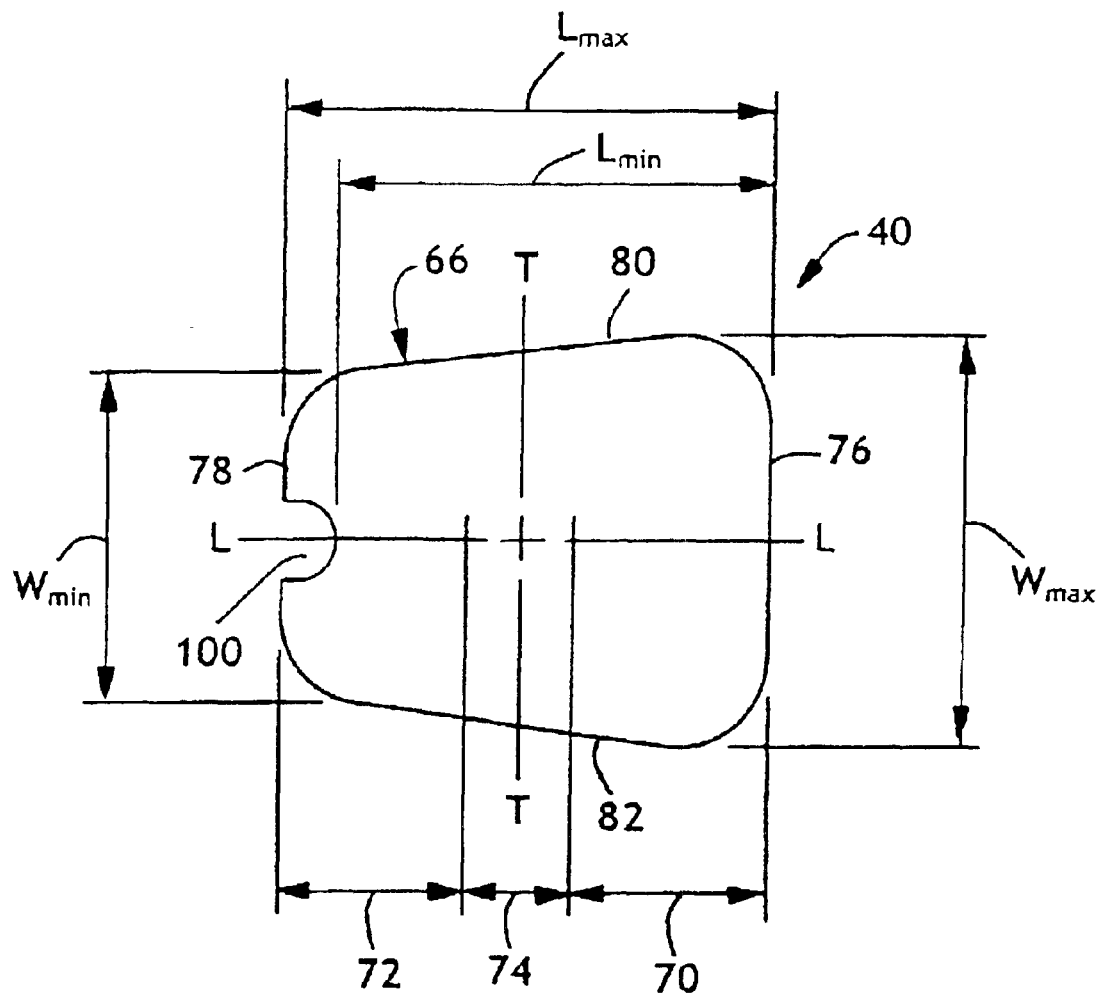
Figure 8:
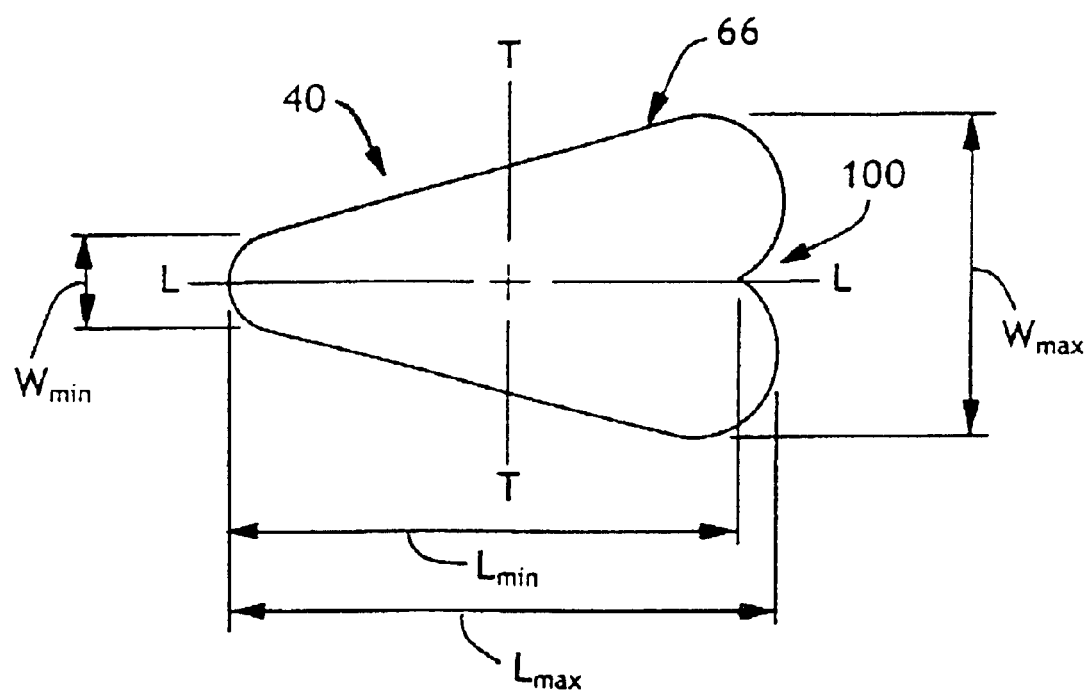
Figure 9:
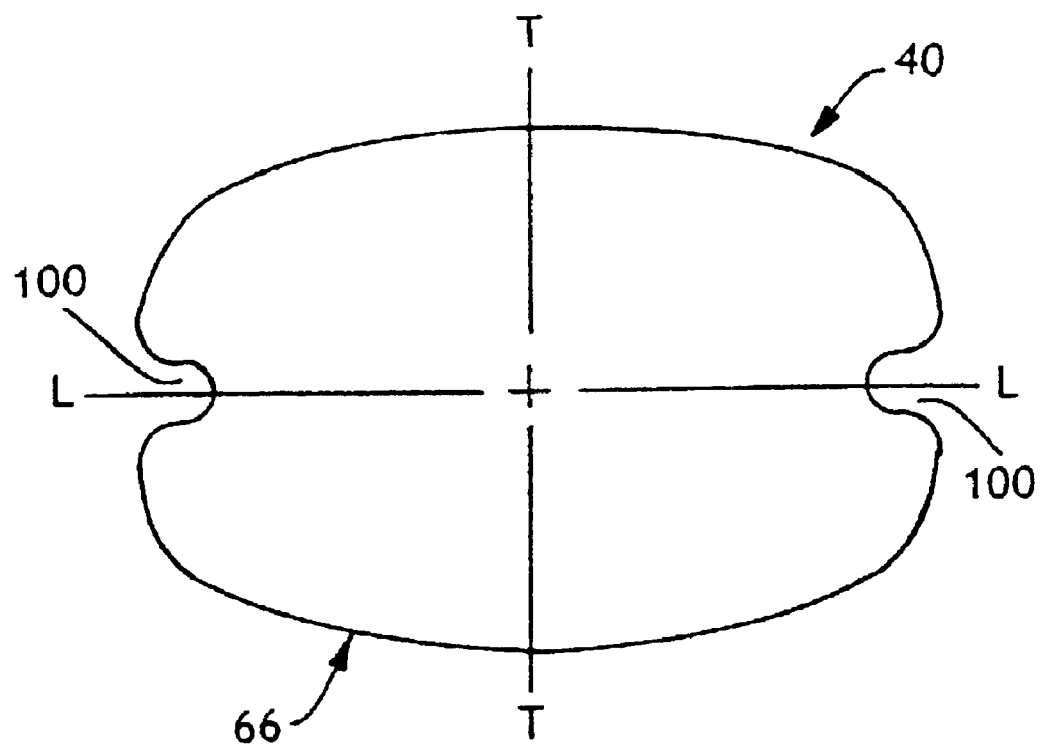
Figure 10:
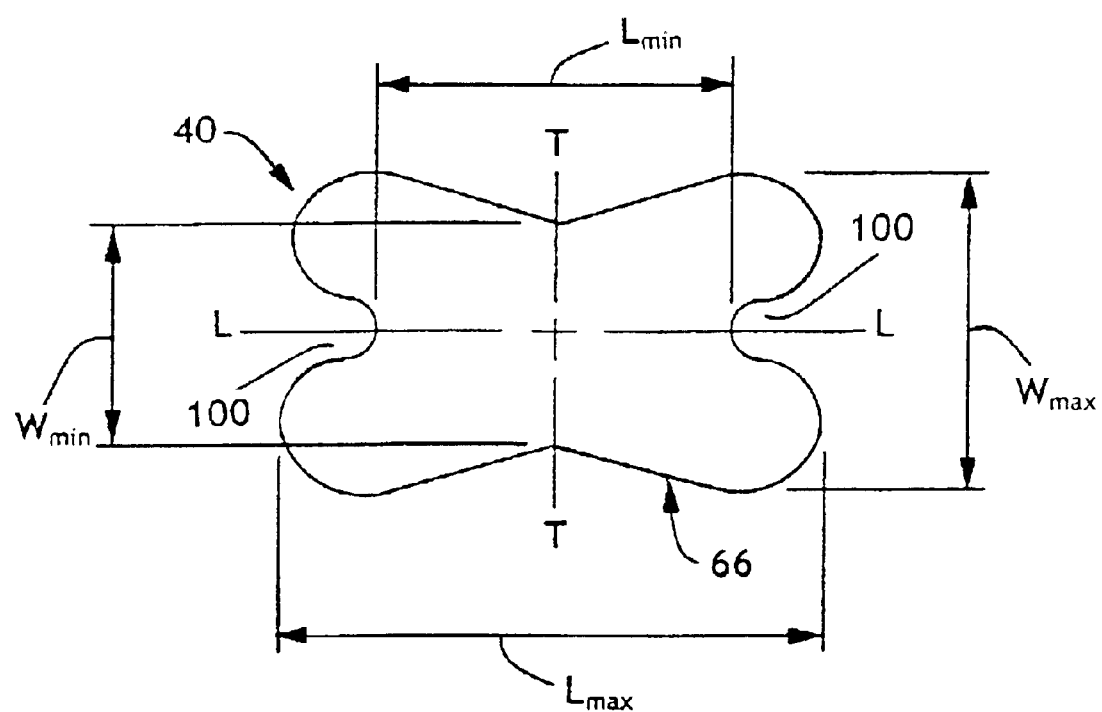

As illustrated in FIG. 6, a representative article (e.g. the illustrated interlabial device 40) can include a liquid-permeable cover or topsheet layer 62, a baffle or backsheet layer 64 which may be operatively liquid-impermeable, and a pliable component member 66 which is operatively situated between the cover and the baffle. The pliable component 66 may optionally be configured as an absorbent body or absorbent core, and may have a composite structure. As illustrated in FIG. 7, the pliable component 66 and the article can each have a first end region 70, a second end region 72, and a central region 74 disposed between the first and second end regions 70, 72, respectively. The maintenance article has a suitable size and shape that allow at least a portion of the maintenance article to be disposed within the vestibule 42 of a female wearer. In addition, the article can at least partially occlude and intercept the flow of a selected treatment material, menstrual fluid, urine or other bodily exudate from the wearer's vaginal orifice 56 and/or urethral orifice 58.

The pliable component 66, and thus the maintenance article, can generally display a geometry extending between spaced apart first 76 and second 78 transverse end areas. The overall geometry is completed by noting that the pliable component 66, and thus the maintenance article, also includes spaced apart first 80 and second 82 longitudinal sides ranging between the transverse end areas 76, 78, these collectively sometimes being referred to herein as the perimetric sides i.e., those defining the periphery.

The geometry of the pliable component 66 can be a significant factor affecting the overall size and effectiveness of the maintenance article (e.g. the interlabial device 40). In general, the pliable component 66 can have a maximum width ($W_{max}$), measured along a line laying generally parallel to the principal transverse axis (T) and running from one longitudinal side 80 to the opposing longitudinal side 82, and a minimum width ($W_{min}$) measured along a second line which also lies generally parallel to the principal transverse axis (T) and runs from one longitudinal side 80 to the opposing longitudinal side 82. Thus, the pliable component 66 may have a width ranging between a minimum of no less than about 5 mm, up to a maximum of about 70 mm; although the approximate widths of the pliable member may vary according to, inter alia, the general design and intended disposition of the maintenance article within the vestibule 42 of a female wearer. One of skill in the art will readily appreciate that certain versions of the pliable component 66, and thus certain versions of the maintenance article, may have a minimum width ($W_{min}$) equal to its maximum width ($W_{max}$). In such instances, reference is generally made only to the maximum width ($W_{max}$).

The pliable component 66 can have a maximum length ($L_{max}$), measured along a line laying generally parallel to the principal longitudinal axis (L) and running from one transverse end area to the other transverse end area 76, 78. Thus, the pliable component 66 may have a length ranging between no less than about 40 mm up to no greater than about 100 mm; although the approximate lengths of the pliable member 66 may vary according to, inter alia, the general design and intended disposition of the maintenance article within the vestibule 42 of a female wearer. One of skill in the art will readily appreciate that certain versions of the pliable component 66, and thus certain versions of the maintenance article, may have a minimum length ($L_{min}$) equal to its maximum length ($L_{max}$). In such instances, as illustrated at least in FIG. 4, reference is generally made only to the maximum length ($L_{max}$). Versions of a pliable component 66, and thus versions of a maintenance article, having a maximum length ($L_{max}$) not equal to its minimum length ($L_{min}$) are illustrated at least in FIGS. 7 through 10 and FIG. 15.

Similar to the pliable component 66, the maintenance article 40 can have a maximum width of up to about 70 mm, and can have a maximum length of up to about 100 mm. Additionally, the maintenance article can have a minimum width of not less than about 5 mm, and a minimum length of not less than about 70 mm.

The first end region 70 and the second end region 72 each minimally extend outwardly from the central region 74 toward the transverse end areas 76 and 78, respectively of the pliable component 66 a distance of no less than about 30; alternatively, no less than about 20; or alternatively, no less than about 10% of the maximum length ($L_{max}$) of the pliable component. The first end region 70 and the second end region 72 each maximally extend outwardly from the central region 74 toward the transverse end areas 76 and 78, respectively of the pliable component 66 a distance of no greater than about 20; alternatively, no greater than about 30; or alternatively, no greater than about 40% of the maximum length ($L_{max}$) of the pliable component. Thus, the end regions 70, 72 may occupy from a minimum of about 20% up to a maximum of about 80% of the maximum length ($L_{max}$) of the pliable component 66; although the approximate size of the first and second end regions may vary according to, inter alia, the general design and intended disposition of the maintenance article within the vestibule 42 of a female wearer.

The maintenance article (such as provided by the interlabial device 40) may optionally be configured with sufficient capacity to absorb and retain an intended amount and type of bodily fluids or exudates. The absorbent capacity may be provided by the pliable member 66, or may be provided by a liquid-retentive member or absorbent core. The absorbent core may be a part of the pliable member 66, or may be a separately provided component that is additional to the pliable member. In a particular feature, the absorbent can be a closely-formed structure or a relatively closed structure with a relatively small pore structure. Additionally, the absorbent can be configured to preferentially retard an absorption of the selected treatment material 86. For a selected bodily fluid, such as urine or menstrual fluid, the pliable component 66 or other absorbent member may have a minimum absorbent capacity of no less than about 1 gram of liquid per gram of the absorbent (1 g/g), and may have a maximum capacity of about 30 g/g or more; although the approximate capacity of the absorbent may vary according to, inter alia, the general design and intended disposition of the maintenance article within the vestibule 42 of a female wearer. One of skill in the art will readily realize that superabsorbent polymers or coated superabsorbent polymers can be added to the pliable component 66 to thereby substantially increasing the absorbent capacity.

In a particular aspect, the pliable component can be configured to have a relatively low absorbency with regard to the selected treatment material, and can be configured to be substantially non-absorbent with regard to the treatment material. In another aspect, the maintenance article, and more particularly the pliable component 66, may have a total absorbent capacity of not more than a maximum of about 1 gram of the selected treatment material. The article or pliable component may alternatively have an absorbent capacity that is not more than about 0.5 gram of the selected treatment material, and may optionally have an absorbent capacity that is not more than about 0.2 gram of the selected treatment material to provide desired performance.

Figure 11:
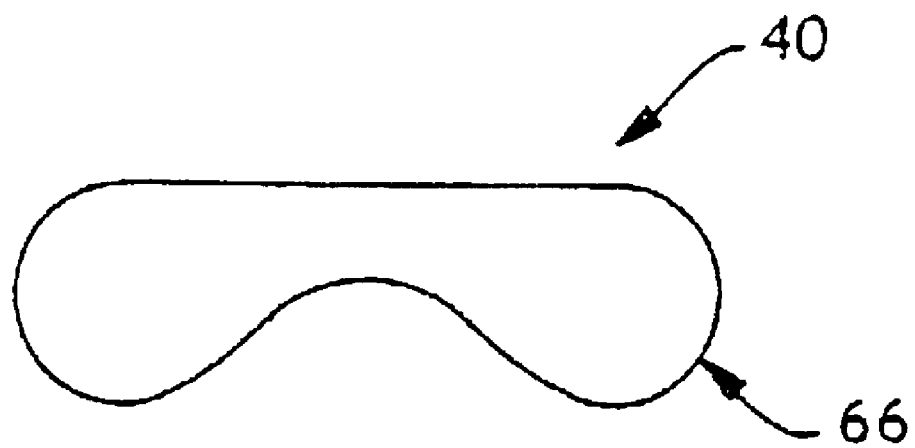

The pliable component 66 has an upper or body-facing surface and a lower surface or surface opposed to the upper or body-facing surface and may include a material capable of absorbing and/or adsorbing and thereafter retaining one or more bodily exudates. Suitable materials can also be generally hydrophilic, compressible, moldable and/or conformable. The pliable component 66 may be formed from any of the materials well known to those of ordinary skill in the art. Examples of such materials include, but are not limited to, various natural or synthetic fibers, multiple plies of creped cellulose wadding, fluffed cellulose fibers, rayon or other regenerated cellulose materials, wood pulp fibers or comminuted wood pulp fibers, airlaid material, textile fibers, a blend of polyester and polypropylene fibers, absorbent foams, absorbent sponges, superabsorbent polymers, coated superabsorbent polymers, fibrous bundles or nits, or any equivalent material or combination of materials. Also suitable for use would be hydrophobic material that has been rendered hydrophilic according to any of a number of known methods for so doing. The total absorbent capacity of the pliable component 66 should, however, be compatible with the design exudate loading and the intended use of the maintenance article. Further, the size and absorbent capacity of the pliable component 66 may be varied. Therefore, the dimension, shape, and configuration of the pliable component 66 may be varied e.g., the absorbent may have a varying thickness, as illustrated at least in FIGS. 11 and 12, or may have a hydrophilic gradient, or may contain superabsorbent polymers and the like.

The pliable component 66 generally has a thickness, caliper or height H, as illustrated at least in FIG. 5, measured along a line lying generally parallel to the z-axis. The minimum thickness of the pliable component 66 typically is no less than about 0.5 mm. Additionally, the pliable component 66 may have a maximum thickness of up to about 10 mm or more; although the approximate thickness of the absorbent may vary according to, inter alia, the general design and intended disposition of the maintenance article within the vestibule 42 of a female wearer.

The pliable component 66 can also have a relatively low density to help provide improved comfort. Generally, the absorbent can have a maximum density of not more than about 0.5 g/cm$^3$. The pliable component 66 can also has a minimum density of no less than about 0.01 g/cm$^3$. Additionally, the approximate density of the absorbent may vary according to, inter alia, the general design and intended disposition of the maintenance article within the vestibule 42 of a female wearer.

The pliable component 66 can have a maximum basis weight of up to about 600 grams per square meter (gsm). The pliable component 66 can also have a minimum basis weight of no less than about 0.1 g/m$^2$. Additionally, the approximate basis weight of the absorbent may vary according to, inter alia, the general design and intended disposition of the maintenance article within the vestibule 42 of a female wearer. A particular example of a suitable absorbent would be similar to a coform material made of a blend of polypropylene and cellulose fibers which has been employed in KOTEX brand, maxi-pantiliners and are obtainable from Kimberly-Clark Corporation, Neenah, Wis., U.S.A.

Various materials may be employed to form the pliable component or member 66. In desired configurations, the materials are operatively moldable and shapeable. Such materials can include, for example, open-cell or closed-cell foam materials, sponge materials, fibrous materials, gel materials, absorbent particles, adsorbent particles or the like, as well as combinations thereof.

The optional backsheet layer or baffle 64 typically resides on the lower surface of the pliable component 66, and may be constructed from any desired material. In a particular arrangement the backsheet or baffle layer 64 may be configured to be operatively liquid-impermeable. Desirably, the baffle 64 can be configured to be breathable. Accordingly, the baffle can permit the passage of air and moisture vapor out of the pliable component 66, while blocking the passage of bodily liquids. An example of a suitable baffle material is a micro-embossed, polymeric film, such as polyethylene, polypropylene or polyester, having a minimum thickness of no less than about 0.025 mm and a maximum thickness of no greater than about 0.13 mm. Bicomponent films can also be used, as well as woven and nonwoven fabrics which have been treated to render them liquid-impermeable. An example of another suitable material is a closed cell polyolefin foam. A closed cell polyethylene foam may also work well.

The baffle 64 may be maintained in secured relation with the pliable component 66 by bonding all or a portion of the adjacent surfaces to one another. A variety of bonding methods known to one of skill in the art may be utilized to achieve any such secured relation. Examples of such methods can include, but are not limited to, ultrasonics, thermal bonding, or the application of adhesives in a variety of patterns between the two adjoining surfaces. A specific example of a baffle material would be similar to a polyethylene film used on KOTEX brand pantiliners and obtainable from Pliant Corporation, Schaumburg, Ill., U.S.A.

The optional topsheet or layer cover 62 has an upper surface and a lower surface, with the upper surface typically configured to contact the body of the wearer and to receive bodily exudates. Additionally, the cover may be configured to be operatively liquid-permeable. The cover 62 desirably is made of a material that is flexible and non-irritating to the tissues within the vestibule 42 of a female wearer. As used herein, the term "flexible" is intended to refer to materials which are compliant and readily conform to the bodily surfaces or respond by easily deforming in the presence of external forces.

The cover 62 can be configured to provide conformability and comfort to the wearer, and may optionally be configured to direct bodily exudates away from the wearer's body and toward the pliable component 66. The cover 62 should desirably retain little or no liquid in its structure, is desirably configured to provide a relatively comfortable and non-irritating surface next to the body tissues within the vestibule 42 of a female wearer. The cover 62 can be constructed of any operative material, such as provided by a film material, woven material, nonwoven material or the like, as well combinations thereof. Additionally, the cover can be configured to be easily penetrated by bodily liquids that contact the surface of the cover. Examples of suitable materials include rayon fabric, bonded carded webs of polyester, polypropylene, polyethylene, nylon, or other heat-bondable fibers, polyolefin materials, such as copolymers of polypropylene and polyethylene, linear low-density polyethylene, aliphatic esters such as polylactic acid, polymer films, finely perforated film webs, net material or the like, as well as combinations thereof. A specific example of a suitable cover material can be similar to a bonded carded web made of polypropylene and polyethylene that has been used as a cover stock for KOTEX brand pantiliners and has been obtained from Sandler Corporation, Germany. Other examples of suitable materials are composite materials of a polymer and a nonwoven fabric material. The composite materials are typically in the form of integral sheets generally formed by the extrusion of a polymer onto a web of spunbond material. The liquid-permeable cover 62 can optionally contain a plurality of apertures (not shown) that are formed partially or completed through the z-directional thickness of the cover layer. The apertures can, for example, increase the rate at which bodily fluids penetrate into the pliable component 66.

In a particular feature, the cover 62 may be configured to have a relatively low permeability with respect to the selected treatment material. Optionally the cover may be configured to be substantially impermeable to the selected treatment material to provide improved performance.

A physiologically hydrous cover material may also be employed. As used herein, the term "physiologically hydrous" is intended to connote a cover material which maintains a suitably moist interface between the tissues of the vestibule 42 and the maintenance article when disposed in that vestibular environment; one that is benign respecting the requirements of comfort associated with the interposition of fabric or fabric-like structures within the moist body-tissue environment of the vestibule, keeping in mind the fact that the maintenance article may be receiving bodily fluids migrating through the vestibule and may be arranged to conduct such bodily fluids to the pliable component 66 or other employed absorbent member. Thus, while not "hydrous" in the classic sense prior to use inasmuch as the cover will be dry at that time the cover 62 maintains or at least does not interfere with the maintenance of the proper moisture level or balance required within the vestibule 42.

The cover 62 can also have at least a portion of its surface treated with a surfactant to render the cover more hydrophilic. This can permit the incoming bodily fluids to more readily penetrate the cover 62. The surfactant may also diminish the likelihood that the incoming bodily fluids, such as menstrual fluid, will flow off the cover 62 rather than being absorbed by the pliable component 66. The surfactant can be irregularly or discontinuously applied to the upper surface of the cover 62 that overlays the upper surface of the pliable component 66. The surfactant can alternatively be substantially evenly distributed across at least a portion of the upper surface of the cover that overlays the upper surface of the pliable component.

The cover 62 may be maintained in secured relation with the pliable component 66 by bonding all or a portion of the adjacent surfaces to one another. A variety of bonding methods known to one of skill in the art may be utilized to achieve any such secured relation. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 62 typically resides on the upper surface of the pliable component 66, but alternatively can surround and partially or entirely enclose the absorbent. Alternatively, the cover 62 and the baffle 64 can have peripheries which extend outwardly beyond the periphery of the pliable component 66 and can be peripherally joined together to form an outboard edge region 84, as illustrated at least in FIG. 6. Utilizing known techniques, such as, for example, gluing, crimping, hot-sealing or the like, the edge region 84 may be formed entirely, so that the entire periphery of the pliable component 66 is circumscribed by their joinder. Alternatively, the cover 62 and the baffle 64 can be partially peripherally joined along selected portions of the entire periphery. To minimize the possibility of irritation and/or discomfort to the wearer of the maintenance article, it is desired that the edge region 84 and at least the area of the maintenance article immediately adjacent the edge be soft, compressible and conformable. Desirably, the edge region 84 can have a minimum width of no less than about 0.5 mm, and can have a maximum width of up to about 10 mm. Additionally, the approximate width of any edge portion may vary according to, inter alia, the general design and intended disposition of the maintenance article within the vestibule 42 of a female wearer. In other optional embodiments, the cover 62 and/or the baffle 64 can have a periphery that is substantially coterminous with the periphery of the pliable component 66.

Positioned either on or substantially parallel to the principal longitudinal axis (L) of the pliable component 66, there may optionally be a desired axis of flexure. A desired axis of flexure generally runs in the longitudinal direction, i.e., along the x-direction, and may be off center from the principal longitudinal axis (L) by a selected distance. Desirably, the desired axis of flexure is aligned along the principal longitudinal axis (L). Additionally, the axis of flexure can extend about 40–100% of the maximum length ($L_{max}$) of the pliable component 66. A desired axis of flexure may result naturally from the dimensions, shape, and/or configuration of the pliable component 66, or the pliable component may be imparted with a weakened axis or region to create a desired axis of flexure. A desired axis of flexure may also be formed by any of the techniques known to one of skill in the art, including, for example, scoring, pre-folding, slitting, embossing, or the like. Although a desired axis of flexure is described herein as residing in the pliable component 66, one of skill in the art will readily appreciate that a desired axis of flexure may be formed in the cover 62, the baffle 64 and/or the absorbent; the cover and the baffle; the cover and the absorbent; or the baffle and the absorbent. When present, a desired axis of flexure typically allows a maintenance article (e.g. the interlabial device 40) to be folded more easily prior to disposition within the vestibule 42 of a female wearer.

The maintenance article also has a thickness, caliper or height H, as illustrated at least in FIGS. 5 and 6, measured along a line laying generally parallel to the z-axis. The minimum thickness of the maintenance article can be not less than about 0.5 mm; and the maximum thickness can be up to about 10 mm; although the approximate thickness of the maintenance article may vary according to, inter alia, the general design and intended disposition of the maintenance article within the vestibule 42 of a female wearer.

Figure 12:
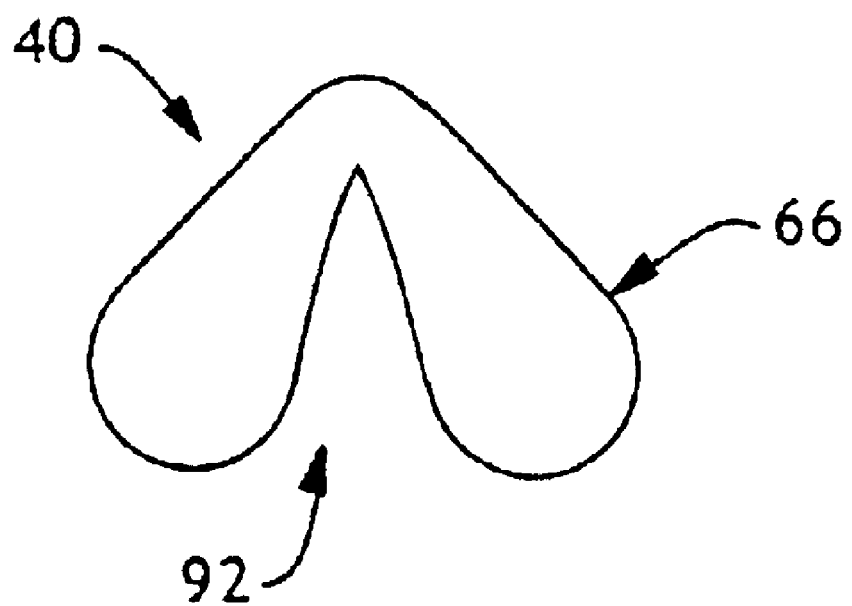
Figure 13:
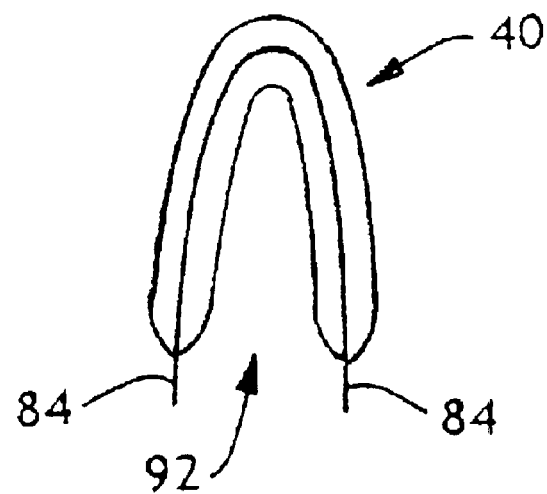
FIG. 13 illustrates a representative, enlarged view of another version of a maintenance article folded substantially about a principal axis.
Figure 14:
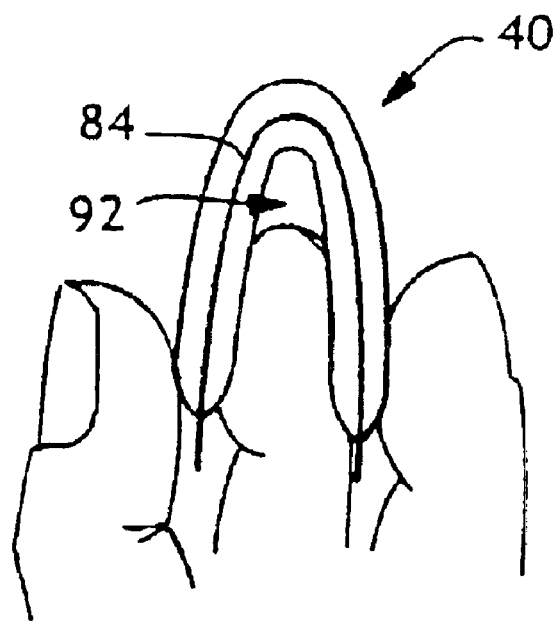
FIG. 14 illustrates a representative, exaggerated enlarged view of an article folded substantially about a principal axis and being grasped for disposition in the vestibule by the wearer's fingers.

The maintenance article (e.g. the interlabial device 40) can optionally be configured to be folded along an axis lying on or positioned parallel to the principal longitudinal axis (L), as illustrated at least in FIGS. 12, 13 and 14, prior to disposition within the vestibule 42 of the female wearer. When folded along such an axis, the maintenance article will form a recess 92 which protects the wearer's fingers from soiling when the maintenance article is disposed within the vestibule 42. Once inserted, the maintenance article may have a tendency to unfold in an attempt to fill the vestibule and thus maintain the upper surface of the maintenance article in contact with the body tissues of the vestibule 42. The maintenance article may be resiliently biased along the axis about which it is folded to increase the tendency of the maintenance article to unfold. Alternatively, the pliable component 66 of the maintenance article may be thicker along its longitudinal edges, as illustrated at least in FIGS. 12 and 13, thus also demonstrating a biasing effect, if desired, which is typically intended to allow the upper surface of the maintenance article to contact the tissues of the vestibule 42. A maintenance article as described herein, however, does not necessarily require any additional features to maintain contact with the body tissues of the vestibule 42 of the female wearer. The naturally moist surfaces of the tissues of the vestibule 42 typically demonstrate a tendency to maintain contact with the upper surface of the maintenance article.

As noted above, the wearer may fold the maintenance article along an axis lying on or positioned parallel to the principal longitudinal axis (L) prior to disposition within the vestibule 42. The wearer may, therefore, hold the folded maintenance article at the longitudinal sides as illustrated at least in FIG. 14. The maintenance article may then be disposed within the vestibule 42 by the wearer exerting a force with a finger or fingers positioned in the recess 92 formed by the folded maintenance article.

As illustrated at least in FIGS. 3, 7 through 10 and 15, the pliable component 66, and thus the maintenance article, may be provided with at least one notch 100 extending inward from the periphery. As used herein, the term "notch" refers to a space, indentation or hollow region along the periphery of a material, a layer of material, a laminate of materials or other composite of materials. Because of the numerous possible geometries for the pliable component 66, and thus the maintenance article, it is almost impossible to indicate where on a particularly configured maintenance article the notch 100 should be located without seeing that particular maintenance article in use. However, it has been determined that when located at least in the periphery of that portion of the maintenance article that is to be situated nearest the clitoris 60, the notch 100 can help maximize the possibility that the maintenance article will maintain a substantially spaced relationship from a female wearer's clitoris when the maintenance article is disposed in a female wearer's vestibule 42. Such a spaced relationship can help minimize the likelihood that the maintenance article will contact the sensitive clitoris 60, thus guarding against the irritating and perhaps painful chafing effects which can arise from excessive contact between the clitoris and the maintenance article.

Additionally, the desired incorporation of the notch region in the maintenance article, and the desired placement of the notch region in a position close to the clitoris can allow the wearer to better control the use of the maintenance article. In a particular aspect, the notch region can be configured to substantially avoid placement over the wearer's urethra during ordinary and customary use. Thusly configured, the maintenance article can more effectively remain in position in the vestibule during and after urination. As a result, the wearer can have more control over when the maintenance article is removed and/or replaced. Additionally, the maintenance article will not be automatically or uncontrollably discharged from the vestibule during urination and require replacement. The increased control over the discharge of the maintenance article can render the article more convenient and more economical to use.

It has also been determined that when a notch region 100 is located at least in the periphery of that portion of the maintenance article to be situated nearest the perineum 50, the notch can help minimize the likelihood that the maintenance article will come into irritating contact with the sensitive perineal region. This is believed to be significant for those wearers who would use the maintenance article post-partum when the perineal region is highly sensitized or has been sewn due to tearing or having been cut during childbirth. It is noteworthy, however, that even those wearers who are nulliparous, i.e., the perineal region has not been exposed or experienced stretching, tearing or cutting during childbirth, may also have highly sensitive perineal regions.

The pliable component 66, and thus the maintenance article, may include at least one notch 100 extending inward from the periphery of at least one of the transverse end areas 76, 78. The notch 100 may, for example, be situated substantially on or adjacent to the principal longitudinal axis (L) of the pliable component 66. Alternatively, the notch 100 may be situated substantially on or adjacent to a desired axis of flexure. The notch 100 may also provide a natural folding or bending line to the pliable component 66 thus allowing the maintenance article, when folded or bent along any such line, to be more easily folded or bent. This is believed to be particularly true when a pliable component 66 (e.g. as illustrated at least in FIGS. 9, 10 and 15) has at least one notch 100 situated in the periphery of each opposing transverse end area 76, 78. As illustrated, the pliable component 66 and/or the article can have at least two notches 100 situated in the article periphery. For example, there can be one notch at or near opposing ends of an axis or line of the article (e.g. FIG. 16). When the maintenance article is disposed within the vestibule, and when the notch 100 is located at least in the periphery of the transverse end area that is to be situated nearest the clitoris 60, the configuration can help minimize the likelihood that the maintenance article will irritatingly contact the sensitive clitoris.

Although previously described herein as capable of being optionally folded along an axis lying on or positioned parallel to the principal longitudinal axis, the maintenance article (e.g. the interlabial device 40) may also be folded along an axis lying on or positioned parallel to the principal transverse axis (T) prior to disposition within the vestibule 42 of the female wearer. When folded along such an axis, the maintenance article typically still forms a recess 92 which protects the wearer's fingers from soiling when the maintenance article is disposed within the vestibule 42. Once inserted, the maintenance article may have a tendency to unfold in an attempt to fill the vestibule and thus maintain the upper surface of the maintenance article in contact with the tissues of the vestibule 42. The maintenance article may be resiliently biased along the axis about which it is folded to increase the tendency of the maintenance article to unfold. Alternatively, the pliable component 66 of the maintenance article may be thicker along its transverse end areas 76, 78 thus also demonstrating a biasing effect, if desired, which is typically intended to allow the upper surface of the maintenance article to contact the tissues of the vestibule 42. A maintenance article as described herein, however, does not necessarily require any additional features to maintain contact with the tissues of the vestibule 42 of the female wearer. The naturally moist surfaces of the tissues of the vestibule 42 typically demonstrate a tendency to maintain contact with the upper surface of the maintenance article.

In another version, a pliable component 66, and thus a maintenance article, includes at least one notch 100 extending inward from the periphery of at least one of the longitudinal sides 80, 82. The notch 100 may, for example, be situated substantially on or adjacent to the principal transverse axis (T) of the pliable component 66. The notch 100 may also provide a natural folding or bending line to the pliable component 66 thus allowing the maintenance article, when folded or bent along any such transverse axis or line, to be more easily folded or bent. This is believed to be particularly true when a pliable component 66, a version of which is illustrated at least in FIG. 10, has at least one notch 100 situated in the periphery of each opposing longitudinal side 80, 82. When the maintenance article is disposed within the vestibule, the notch 100, when located at least in the periphery of the longitudinal side to be situated nearest the clitoris 60, minimizes the likelihood that the maintenance article will irritatingly contact the sensitive clitoris.

Desirably, the notch 100 is of dimensions sufficient to minimize the likelihood that the maintenance article will, when appropriately disposed within a female wearer's vestibule 42, come into irritating contact with the clitoris 60 and/or the perineum 50, as desired. Stated differently, the notch 100 desirably is of dimensions sufficient to maximize the possibility that the maintenance article will maintain a substantially spaced relationship from the clitoris 60 and/or the perineum 50, as desired, when the maintenance article is appropriately disposed within a female wearer's vestibule 42.

The notch 100 suitably extends inward from the periphery of the pliable component 66 by a depth, as measured approximately perpendicularly from the peripheral, terminal edge of the absorbent, For example, the notch 100 may have a minimum depth of no less than about 2 mm, and may have a maximum depth of up to about 30 mm; although the approximate depth of the notch may vary according to, inter alia, the general design and intended disposition of the maintenance article within the vestibule 42 of a female wearer.

The notch 100 also has a width, the widest portion of which is typically situated at least along the periphery of the pliable component 66. Desirably, the notch 100 has a maximum width of up to about 30, and a minimum width of not than about 0.5 mm; although the approximate width of the notch may vary according to, inter alia, the general design and intended disposition of the maintenance article within the vestibule 42 of a female wearer.

The notch 100 when configured as described herein may have a variety of geometries including U-shaped, V-shaped, W-shaped, semi-circular or a variety of combinations thereof. Several examples of possible notch 100 geometries are illustrated in several of the Figures. One of skill in the art will recognize, however, that the notch geometries identified herein are non-limiting and are but a few examples of the many geometries that may be suitable for the notch 100 described herein.

The notch 100 of the present invention may be situated on the periphery of a pliable component 66, and thus the periphery of a maintenance article, having a variety of geometries. Examples of such geometries of the article and of the components of the article can include, but are not limited to, rectangular, ovoid-like, elliptical, trapezoidal, circular, semi-circular, triangular, square-shaped, teardrop-like, diamond-shaped, polygonal-shaped, butterfly, pear-shaped, heart-shaped, or the like, as was well as any operative combination thereof.

Suitable interlabial devices are also described in U.S. patent application Ser. No. 10/036,981 entitled LABIAL PAD HAVING A TAB by Heather A. Sorebo et al. which was filed Dec. 31, 2001 (attorney docket No. 17,692). The entire disclosure of this document is incorporated herein by reference in a manner that is consistent herewith.

Figure 15:
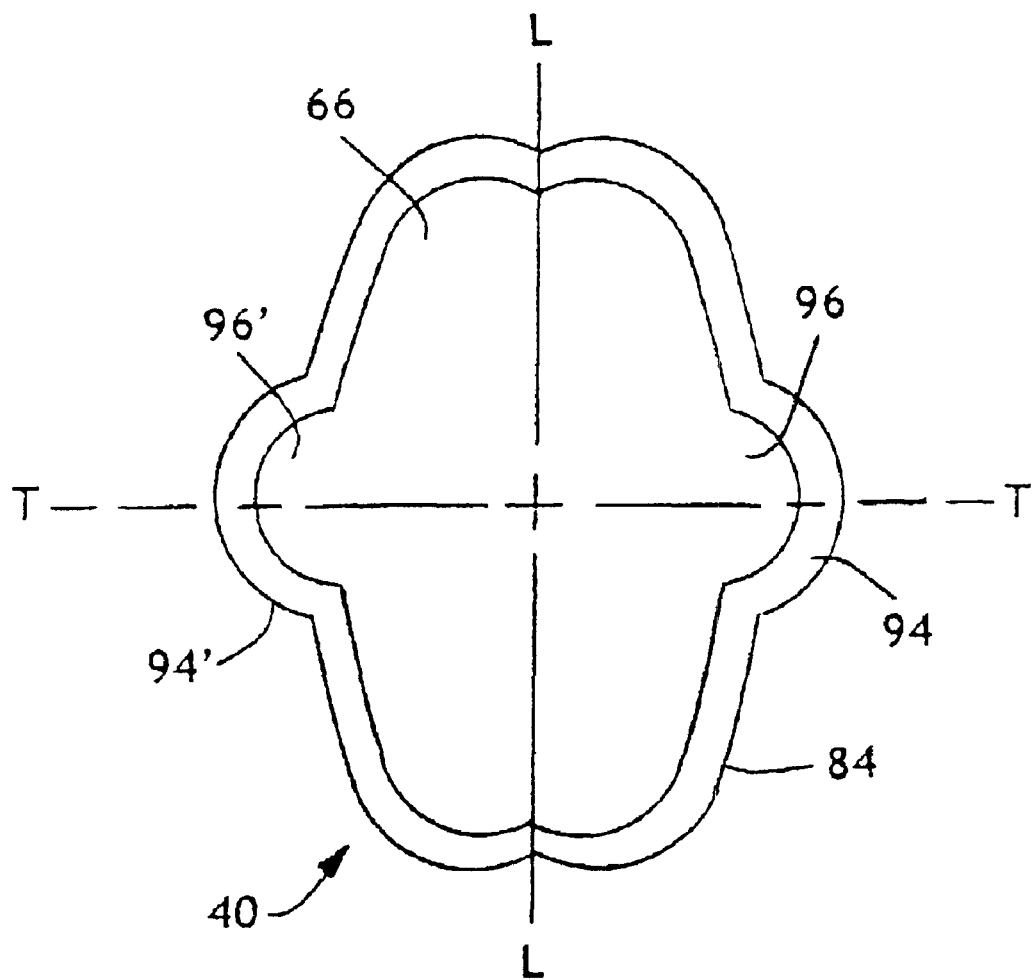
FIG. 15 shows a maintenance article which is arranged in a generally flat condition and has a representative system of one or more tab regions.
Figure 16:
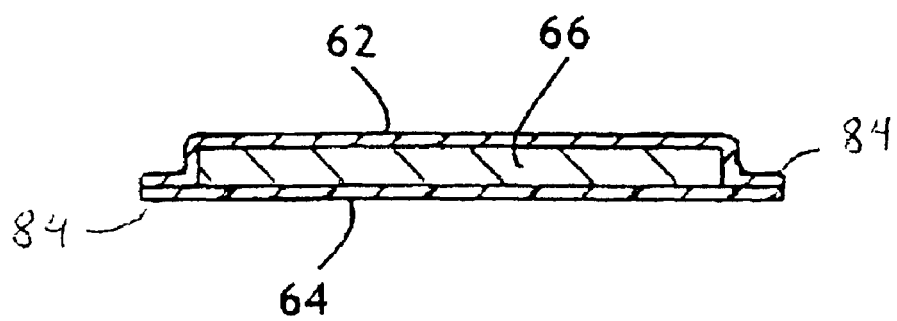
FIG. 16 shows a representative cross-section through a maintenance article having one or more tab regions.

With reference to FIGS. 15 and 16, the maintenance article (e.g. such as provided by the interlabial device 40) can include at least one, placement and removal tab region 94 which extends outward from at least one longitudinal side 80, 82 of the maintenance article. Each tab region may or may not include absorbent material, as desired. While one such tab 94 may conceptually work effectively in the placement and removal of a maintenance article such as a labial pad, it is believed that at least two tabs 94 and 94', i.e., one tab extending from each longitudinal side 80, 82 of the maintenance article, can be more effective in the placement and removal of a maintenance article. Consequently, in the discussion that follows, unless otherwise noted, the maintenance article can have at least two tabs 94, 94'. While it is not necessary, the tabs 94, 94' can be identical, or more properly, mirror images each other. Thus, the description of the first tab will be a corresponding description of any other tab. Discussion of any other tab will, therefore, be omitted for clarity of exposition. Corresponding elements are indicated in the drawings by reference numerals and primed reference numerals.

Extending outward from a longitudinal side 80, 82 of a maintenance article, the tab 94 can be of any suitable configuration. Non-limiting examples of shapes for the tab 94 include: ovoid, elliptical, trapezoidal, rectangular, triangular, diamond-shaped, circular, semi-circular, or the like, as well as any combination thereof. The tab 94 may be integrally formed with the maintenance article or it may be a separately provided element that is joined to the maintenance article. One of skill in the art will readily appreciate that when the tab 94 is a separate element joined to the maintenance article, the tab may be so joined by a number of known methods including melt fusion, adhesion, or other joining means. The phrase "integrally formed" is intended to indicate that the tab 94 is a continuous extension of the cover 62, the baffle 64, the pliable component 66 or a like component, as well as a continuous extension of a combination of such components.

The tab 94 has a length measured along a line laying generally parallel to the principal longitudinal axis (L) of a maintenance article, and a width, measured along a line laying generally parallel to the principal transverse axis (T) of a maintenance article. The tab 94 has sufficient dimensions to aid the female user in disposition of the maintenance article within the vestibule 42 and, optionally, removal of the maintenance article from the vestibule. The phrase "sufficient dimensions" is intended to indicate that the tab 94 can be grasped between the index finger and the thumb or, if there are, for example, two tabs, between the index finger and the thumb and the middle finger and the index finger. Typically, the length of the tab 94 is no greater than the maximum length ($L_{max}$) of the pliable component 66. One of skill in the art will readily appreciate that the length of the tab 94 may vary according to, inter alia, the general design and intended disposition of the maintenance article within the vestibule 42 of a female user.

In addition to having a length, the tab 94 also has a width. One of skill in the art will readily appreciate that the width of the tab 94 may vary according to, inter alia, the general design and intended disposition of the maintenance article within the vestibule 42 of a female user.

The dimensions of the tab 94 are limited only by the stress-strain properties of the tab materials. Desirably any material used in the tabs 94, 94' is soft, compressible and conformable and thus similar to the material used in the fluid permeable cover 62, the liquid impermeable baffle 64 and/or the pliable component 66. Any such material is desirably configured to minimize the possibility of irritation and/or discomfort to the wearer of the maintenance article.

The tab 94 of the present invention may be positioned in a variety of locations along the longitudinal side 80, 82 of a maintenance article. With regard to the maintenance articles 40 described herein, the tab 94 may be located in the first end region 70, the second end region 72 or the central region 74. A second tab 94' could at the same time be located along the opposing longitudinal side 80, 82 in the first end region 70, the second end region 72 or the central region 74. Generally, when a tab 94 extends outward from a longitudinal side 80, 82 of a particular region 70, 72, 74, any second tab 94' typically extends outward from the corresponding region 70, 72, 74 of the opposing longitudinal side 80, 82. It should also be noted that, depending on the length of the tab 94, the tab may cover more than one of the regions 70, 72, 74 described herein. The tabs 94, 94' as described herein offer a female wearer the opportunity to grasp the tabs to aid in the disposition of a labial pad into the vestibule. In addition, the tabs 94, 94' also offer a female wearer the opportunity to grasp the tabs to aid in the removal of a labial pad and thus minimize the likelihood that the female wearer's fingers will come into contact with the body-facing surface of the possibly soiled labial pad.

Other suitable interlabial devices are described in U.S. patent application Ser. No. 10/038,973 entitled LABIAL PAD HAVING VARIOUS MEANS by James J. Hlaban et al. which was filed Dec. 31, 2001 (attorney docket No. 17,693). The entire disclosure of this document is incorporated herein by reference in a manner that is consistent herewith.

The pliable component 66 and the maintenance article may, for example, include a placement enhancement structure designed to minimize the surface area of that portion of the maintenance article that comes into contact with the floor 48 of the vestibule 42 when the maintenance article is disposed within the vestibule of a female wearer. Minimizing the surface area of that portion of the maintenance article that comes into contact with the floor 48 of the vestibule 42 is believed to guard against the irritating and perhaps painful chafing effects which contact by a maintenance article with the floor of the vestibule can occasion. For example, the placement enhancement structure can include at least one slit residing on an axis either lying on or running parallel and adjacent to the principal longitudinal axis (L). The placement enhancement structure may include a single continuous slit or a series of slits, and may extend a selected longitudinal distance along the length of the absorbent. For example, the longitudinal distance can have a minimum of no less than about 80% of the length of the pliable component 66, and a maximum of no greater than about 100% of the length of the pliable component 66. Alternatively, the placement enhancement structure can include at least one slit residing on an axis which either lies on or runs parallel and adjacent to the principal transverse axis (T). Accordingly, such a configuration can also include a single slit or a plurality of slits. When the selected configuration of the placement enhancement structure incorporates a series of slits, each slit can be spaced apart from an adjacent slit by a selected spacing distance. For example, the spacing distance can have a minimum of about 2 mm, and a maximum of about 15 mm.

The placement enhancement structure can also have a depth extending through the thickness of the pliable component 66. The approximate length, width, and/or depth of the placement enhancement structure may vary according to, inter alia, the general design and intended disposition of the maintenance article within the vestibule 42 of a female wearer.

In another configuration, the pliable component 66, and the maintenance article, may include a deformation structure which allows the maintenance article to substantially conform to the effective surface area of the vestibule 42 when the maintenance article is folded and disposed therein. The phrase "effective surface area" of the vestibule 42 is intended to refer to that portion of the vestibule that contacts the maintenance article. By substantially conforming to the effective surface area of the vestibule 42 when folded and disposed therein, the maintenance article is less likely to become dislodged away from the vestibule during use. In addition, by substantially conforming to the effective surface area of the vestibule 42, the maintenance article can help minimizes the likelihood of leakage. In a particular arrangement, the deformation structure can include at least one slit, and optionally, a selected plurality of slits, residing on an axis which either lies on or runs parallel and adjacent to the principal longitudinal axis (L). Whether a single continuous slit or a series of slits, the approximate length and/or depth of the deformation means may vary according to, inter alia, the general design and intended disposition of the maintenance article within the vestibule 42 of a female wearer. When incorporating a series of slits, each slit of the deformation structure can be spaced apart from an adjacent slit by a distance of about 2 mm to about 15 mm, If the maintenance article is foldable, a female wearer may optionally fold the article along an axis which lies on or is positioned parallel to the principal transverse axis (T) prior to disposition within the vestibule 42. In such situations, the wearer may, therefore, hold the folded maintenance article at the transverse end areas when disposing the maintenance article within the vestibule 42. Taking into account such instances, the positioning of the deformation structure may be modified accordingly.

In a further arrangement, the pliable component 66, and the maintenance article may include a fluid intake enhancement structure. The fluid intake enhancement structure can contribute to increasing the surface area of the pliable component 66, and can be capable of allowing bodily fluids to be more rapidly absorbed into the pliable component 66, as compared to an identical maintenance article that does not contain such a fluid intake enhancement structure. The fluid intake enhancement structure can allow for rapid absorption of the intended bodily exudate without the typical fluid intake limitations that may be encountered when the upper surface of the pliable component 66 is substantially flat or concave, and is located adjacent the vaginal 56 or urethral 58 orifice. In a particular arrangement, the fluid intake enhancement structure can include at least one slit, and optionally, a plurality of slits, residing on an axis either lying on or running parallel and adjacent to the principal longitudinal axis (L).

Additional examples of interlabial devices are disclosed in U.S. patent application Ser. No. 10/037,276 entitled LABIAL PAD by Ronald L. Edens et al. which was filed Dec. 31, 2001 (attorney docket No. 17,696); and in U.S. patent application Ser. No. 10/038,971 entitled LABIAL PAD by Deanna R. Kathumbi-Jackson et al. which was filed Dec. 31, 2001 (attorney docket No. 17,697). The entire disclosure of this document is incorporated herein by reference in a manner that is consistent herewith.

In addition to considering the length and width of a labial pad or other interlabial device, the surface area of the labial pad or other interlabial device can also play a significant role in enhancing the comfort and fit of a labial pad disposed within a female wearer's vestibule. The effective surface area of the human female vestibule can be as small as about 275 mm$^2$, or even smaller depending on the female. In addition, the effective surface area of the human female vestibule can be as large as about 3,800 mm$^2$, or even larger depending on the female. Use of the phrase "effective surface area" with regard to a vestibule is intended to refer to that portion of the surface of the vestibule available for contact with maintenance articles similar to and including those described herein. Although there exists a great amount of variation in the effective surface area of the human female vestibule, a significant number of human female vestibules can have effective surface areas within the range of about 700 mm$^2$ to about 3,100 mm$^2$. Accordingly, there can be three ranges relative to the differing effective surface areas of female vestibules 42: from about 700 mm$^2$ to about 1,700 mm$^2$; from about 1,700 mm$^2$ to about 2,400 mm$^2$; and from about 2,400 mm$^2$ to about 3,100 mm$^2$. By substantially matching the surface area of the upper surface of a pliable component 66 with the effective surface area of a female wearer's vestibule, the maintenance article can be configured to demonstrate an improved efficacy at maintaining a desired disposition within the vestibule 42. As a result, the maintenance article can provide better coverage of the vestibule, can better minimize the potential for leakage, and can provide enhanced comfort to the wearer. This is particularly significant when desiring to maintain a desired disposition of the maintenance article within the vestibule of a female wearer without the assistance of an additional stay-in-place mechanism, such as, for example, provided by strings, body adhesives, garment adhesives, belts, sanitary napkins, tampons, undergarments or the like.

A process for maintaining a feminine-care treatment can include a providing of an operative quantity of a feminine-care treatment material 86, and a depositing of the treatment material into a vulva-vaginal area of a recipient, female user. A maintenance article, such as provided by an interlabial device 40, can be placed into an interlabial space of the user. The interlabial device or other maintenance article can be arranged to operatively impede an undesired movement of said treatment material 86 from said vulva-vaginal area when the maintenance article is placed in the interlabial space of the user. In a particular configuration, the maintenance article can include a liquid-permeable topsheet layer 62, and a pliable member or component 66 operatively joined to the topsheet layer 62. In a further configuration, an operatively liquid-impermeable backsheet layer 64 can be joined to the topsheet layer, and the absorbent core 66 can be positioned between the topsheet layer 62 and said backsheet layer 64.

With reference to FIGS. 17 through 22A, a system for maintaining a feminine care treatment can include an operative quantity of a feminine care treatment material 86 configured for placement in a vulva-vaginal area of a recipient, female user; and a maintenance article, such as provided by an interlabial device 40, for placement into an interlabial space of the user. The maintenance article is configured to operatively impede a movement of the treatment material 86 from the user's vulva-vaginal area when the interlabial device is placed into the interlabial space of the user.

In a particular aspect, the interlabial device 40 or other maintenance article can include a liquid-permeable topsheet layer 62, and a pliable component or member 66 which is operatively joined with the topsheet layer 86. In another aspect, the interlabial device or other maintenance article can further include an operative, liquid-impermeable backsheet layer 64 which is joined to the topsheet layer 62, with the pliable member 66 positioned between the topsheet layer 62 and the backsheet layer 64. A further aspect of the invention can include a bundling mechanism 90 which operatively holds the treatment material 86 and the maintenance article in a convenient system-assembly 88. In other features, the bundling mechanism may include a first sub-container 102 and a second sub-container 104, and the system-assembly 88 can include an applicator device 96 (e.g. see FIGS. 19 and 19A).

In still another aspect, the feminine-care treatment material 86 can be configured to be a non-absorbent treatment material. Such non-absorbent treatment materials are substantially free of conventional absorbent materials that are employed to absorb aqueous liquids. Accordingly, the non-absorbent treatment materials are substantially free of materials, such as woodpulp fluff, cotton, absorbent cellulosic materials, absorbent synthetic fibers, absorbent natural fibers, absorbent sponges, superabsorbent polymers, and the like. In desired configurations, the treatment material can, for example, be in the form of a liquid, a semi-solid, an ointment, a viscous liquid, a gel, a paste, one or more solid pellets or granules, a powder, or the like, as well as combinations thereof.

Examples of the feminine-care treatment material can include one or more of the following treatment materials: a medicinal agent, such as miconazole nitrate (MONISTAT 7), ketoconazole, metronidazole occlusal-HP, terconazole, other infection treatments or the like; a therapeutic agent, such as vitamins, topical estrogen, micronized testosterone, progesterone, other hormone replacement therapy treatments, sildenafil (VIAGRA), polyvinyprrolidone-iodine; other anti-infective agents; a diagnostic agent; or the like, as well as combinations thereof.

The treatment material 86 and the interlabial device 40 can be distinctively bundled into a system-assembly 88 that is conveniently available for cooperative positioning with the user (e.g. FIGS. 17 through 22A). In a particular aspect, the process and system of the invention can include an arranging of the system-assembly 88 to include at least one operative quantity or dosage of the treatment material 86, and at least one interlabial device. In another aspect, the process and system of the invention can include an arranging of the system-assembly 88 to have a plurality of quantities or dosages of the treatment material 86, and in a further aspect, can include an arranging of the system-assembly 88 to have a plurality of interlabial devices 40. Additionally, the process and system of the invention can further include a bundling mechanism 90 for holding the treatment material 86 and the interlabial device in a convenient system-assembly 88.

Figure 20:
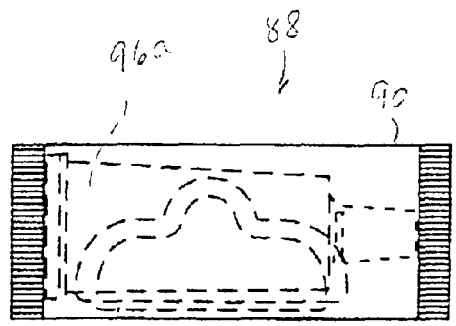
FIG. 20 shows a representative system-assembly 88 that is configured to include at least one individual maintenance article, and a pre-filled applicator provided by a squeeze tube that contains one or more individual quantities or dosages of the selected treatment material.
Figure 21:
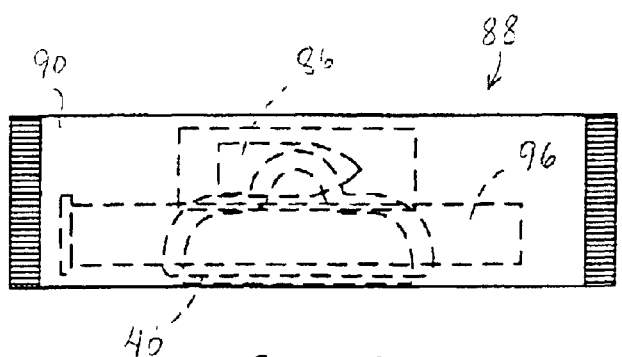
FIG. 21 shows a representative system-assembly which includes at least one individual maintenance article, an applicator, and one or more, separately packaged, individual quantities or dosages of the selected treatment material carried by a selected sub-container.
Figure 21A:
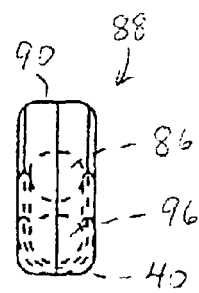
FIG. 21A shows a representative end view of the system-assembly illustrated in FIG. 21.

The process and system can further include an applicator 96 for operatively placing the treatment material 86 in the vulva-vaginal area of the user (e.g. FIGS. 20 through 21A). Accordingly, the system-assembly 88 can be configured to include at least one applicator 96, and optionally, a selected plurality of applicators. Additionally, the selected bundling mechanism 90 can be configured to hold the selected number of applicators in the system-assembly 88, which also contains or otherwise holds the treatment material 86 and the interlabial device(s) 40.

The applicator 96 can include a squeeze tube, a pump device, a syringe, an applicator tube or the like, as well as combinations thereof. In particular aspects, the bundling mechanism 90 can include an adhesive, a shrink-wrap film material, a bundling box, a bundling envelope, a bundling pouch, or the like, as well as combinations thereof.

With reference to FIGS. 17 and 17A, the system-assembly 88 can be arranged to include at least one individual interlabial device 40, and at least one quantity or dosage of treatment material 86. The system-assembly can be operatively held together with a bundling mechanism 90, such as provided by the representatively shown sealed pouch package.

With reference to FIGS. 18 and 18A, the system-assembly 88 can be arranged to include at least one individual interlabial device 40, en applicator 96, and at least one individual quantity or dosage of the selected treatment material 86. The quantity of treatment material may be conveniently preloaded into the applicator, and the system-assembly can be operatively held together with a bundling mechanism provided by the representatively shown sealed pouch. Accordingly, the bundled system-assembly 88 can provide a combined treatment system that is configured into a convenient, total system-package.

With reference to FIGS. 19 and 19A, the system-assembly 88 can be configured to include a plurality of individual interlabial devices 40, a plurality of quantities or dosages of the treatment material 86, and at least one applicator 96. The plurality of individual interlabial devices can be held segregated and separate from the plurality of quantities or dosages of the treatment material. As representatively shown, the plurality of individual interlabial devices 40 can be secured in a first sub-container 102, and the plurality of quantities or dosages of the treatment material can be secured in a second sub-container 104. The sub-containers 102, 104 can be operatively held together with an operative bundling mechanism, such as provided by an adhesive, hook-and-loop fastener, other mechanical fastener, a weld, a thermal bond, an ultrasonic bond, sewn stitches, a shrink-wrap band, an elastic band, perforated film, a system of carton and sub-cartons, or the like, as well as combinations thereof. The sub-containers can be held within a larger container, such as a larger box. The larger container can be constructed to allow a diagonal, separation opening to expose individual, separate items. In a particular arrangement, the larger container can provide for a double-diagonal, "X", separation opening to expose four separately contained items.

In the various configurations of the invention, the predetermined sub-containers can be provided by any operative device or structure. For example, each selected sub-container may be provided by a box, envelope, pouch, bag, carton or the like, as well as combinations thereof.

Figure 20A:
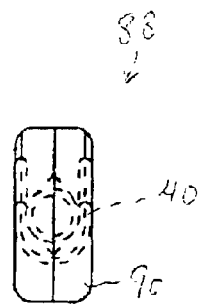
FIG. 20A shows a representative end view of the system-assembly illustrated in FIG. 20.

With reference to FIGS. 20 and 20A, the system-assembly 88 can be arranged to include at least one individual interlabial device 40 or other maintenance article, and a prefilled applicator 96a, such as provided by a squeeze tube that contains one or more individual quantities or dosages of the selected treatment material 86. The system-assembly can be operatively held together with a bundling mechanism provided by the illustrated sealed envelope.

With reference to FIGS. 21 and 21A, the system-assembly 88 can be arranged to include at least one individual interlabial device 40, an applicator 96, and one or more, separately packaged, individual quantities or dosages of the selected treatment material 86. The individual quantities or dosages of the selected treatment material can be separated or segregated by employing a selected sub-container 104. In addition, the system-assembly 88 can be operatively held together with a bundling mechanism which includes the representatively shown pouch, box, and envelope.

Figure 22:
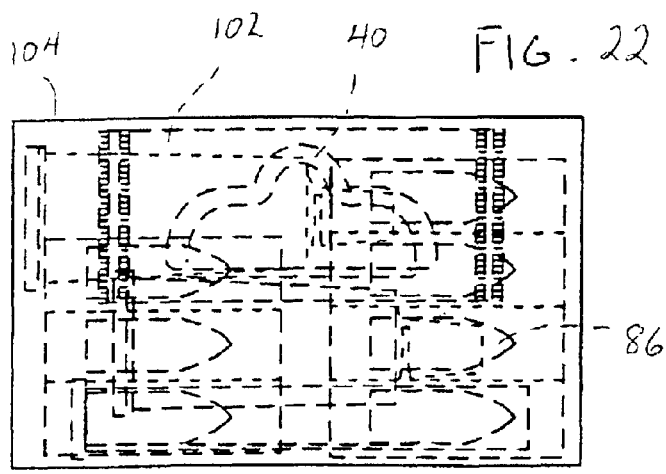
FIG. 22 shows a representative system-assembly which includes a plurality of maintenance articles separately carried by a first sub-container, a first applicator, one or more, separately packaged, individual quantities or dosages of a first selected treatment material, and a second applicator which contains one or more individual quantities or dosages of a second selected treatment material.
Figure 22A:
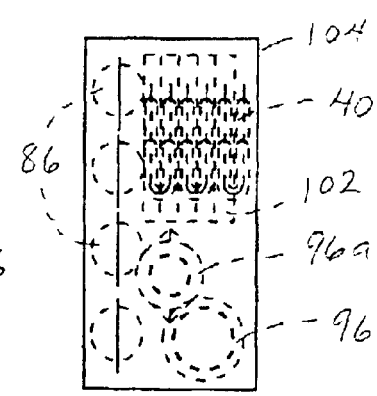
FIG. 22A shows a representative end view of the system-assembly illustrated in FIG. 22.

With reference to FIGS. 22 and 22A, the system-assembly 88 can be arranged to include a plurality of interlabial devices 40, a first applicator 96, and one or more, separately packaged, individual quantities or dosages of a first selected treatment material 86. Additionally, the system-assembly can include a second applicator 96a which contains one or more individual quantities or dosages of a second selected treatment material. The individual interlabial devices 40 can, for example, be separated or segregated by employing a selected sub-container 102, and the individual quantities or dosages of the first treatment material can, for example, be separated or segregated by employing a selected sub-container 104. In addition, the system-assembly 88 can be operatively held together with an operative bundling mechanism, such as provided by the representatively shown combination of pouches, boxes, and envelopes.

Although the present invention has been illustrated and described in considerable detail with reference to certain embodiments thereof, other arrangements and configurations are also possible and are contemplated as being within the scope of the present invention. Therefore, the spirit and scope of the appended claims should not be limited to the illustration and description of the embodiments contained herein.

What is claimed is:

1. A system for maintaining a feminine care treatment, comprising:

an operative quantity of a feminine care treatment material configured for placement in a vulva-vaginal area of a recipient, female user;

an applicator for operatively placing said treatment material in said vulva-vaginal area of the user;

a maintenance article for placement into an interlabial space of said user, said maintenance article configured to operatively impede a movement of said treatment material from the user's vulva-vaginal area when said maintenance article is placed into said interlabial space of the user; and a bundling mechanism for holding said treatment material, said applicator and said maintenance article in a convenient system-assembly;

wherein said maintenance article includes a topsheet layer; and a pliable component which is operatively joined with said topsheet layer;

said maintenance article is provided separate from said feminine care treatment material;

the bundling mechanism holds a plurality of individual maintenance articles, and a plurality of quantities of the feminine care treatment material; and the bundling mechanism holds together a first sub-container which holds the plurality of individual maintenance articles, and a second sub-container which holds the plurality of quantities of the feminine care treatment material.

2. A system as recited in claim 1, wherein said maintenance article has been configured to provide a labial pad.

3. A system as recited in claim 2, wherein said pliable component has been configured with a width of up to about 70 mm and a length of up to about 100 mm, and has been configured to be absorbent.

4. A system as recited in claim 1, further including an operative backsheet layer which is joined to said topsheet layer, and said pliable component is positioned between said topsheet layer and said backsheet layer.

5. A system as recited claim 4, wherein said backsheet layer is configured to be operatively, liquid-impermeable.

6. A system as recited in claim 1, wherein said pliable component is configured to allow a selective shaping to provide a customized fit in said interlabial space of the user.

7. A system as recited in claim 1, wherein said pliable component is configured to provide a low absorbency with regard to said treatment material.

8. A system as recited in claim 1, wherein said pliable component is configured to be operatively absorbent with regard to a bodily exudate.

9. A system for maintaining a feminine care treatment, comprising:

a first plurality of quantities of a first feminine care treatment material configured for placement in a vulva-vaginal area of a recipient, female user;

a second plurality of quantities of a second feminine care treatment material configured for placement in a vulva-vaginal area of a recipient, female user;

a first applicator for operatively placing said first treatment material in said vulva-vaginal area of the user;

a second applicator for operatively placing said second treatment material in said vulva-vaginal area of the user;

a plurality of maintenance articles for placement into an interlabial space of said user, said maintenance article configured to operatively impede a movement of said treatment material from the user's vulva-vaginal area when said maintenance article is placed into said interlabial space of the user; and a bundling mechanism for holding said first and second quantities of treatment material, said first and second applicators and said plurality of maintenance articles in a convenient system-assembly;

wherein each maintenance article includes a topsheet layer, and a pliable component which is operatively joined with said topsheet layer; and each maintenance article is provided separate from said first and second feminine care treatment materials.

10. A system as recited in claim 9, wherein the bundling mechanism holds together a first sub-container which holds the plurality of individual maintenance articles; and a second sub-container which holds the plurality of quantities of the first feminine care treatment material.

* * * * *